United States Patent [19]

Leston

[11] Patent Number: 4,475,001
[45] Date of Patent: Oct. 2, 1984

[54] PROCESS FOR ALKYLATING PHENOLIC COMPOUNDS TO PRODUCE ORTHO- OR PARA-MONOALKYLATED PHENOLS OR 2,4- OR 2,6-DIALKYLATED PHENOLS

[75] Inventor: Gerd Leston, Pittsburgh, Pa.

[73] Assignee: Koppers Company, Inc., Pittsburgh, Pa.

[21] Appl. No.: 476,060

[22] Filed: Mar. 17, 1983

[51] Int. Cl.$^3$ .................. C07C 37/00; C07C 39/06
[52] U.S. Cl. .................. 568/784; 568/780; 568/799; 564/396; 564/442
[58] Field of Search .............. 568/794, 799, 780, 782, 568/784; 564/396, 442

[56] References Cited

U.S. PATENT DOCUMENTS

| | | | |
|---|---|---|---|
| 2,194,215 | 3/1940 | Brunson | 568/780 |
| 2,452,154 | 10/1948 | Ross | 568/780 |
| 2,494,993 | 6/1950 | Foster | 568/780 |
| 2,842,595 | 7/1958 | Rigternik | 568/780 |
| 3,413,347 | 11/1968 | Worrel | 568/780 |
| 3,592,951 | 7/1971 | Zaweski | 568/784 |
| 3,726,882 | 4/1973 | Traise et al. | 568/780 |
| 3,946,086 | 3/1976 | Gershanov et al. | 568/784 |
| 4,072,724 | 2/1978 | Parker | 568/784 |
| 4,122,287 | 10/1978 | Zekharava et al. | 568/784 |
| 4,215,229 | 7/1980 | Greco | 568/784 |
| 4,308,407 | 12/1981 | Melysner et al. | 568/784 |

OTHER PUBLICATIONS

Brunson et al., "J. Amer. Chem. Soc." vol. 63 pp. 270-272 (1941).
Carlin et al., "J. Amer. Chem. Soc." vol. 72 pp. 2762-2763 (1950).
Caldwell et al., "J. Amer. Chem. Soc." vol. 61 pp. 2354-2357.

Primary Examiner—Werren B. Lone
Attorney, Agent, or Firm—Daniel J. Long; Herbert J. Zeh, Jr.

[57] ABSTRACT

Ortho- or para-monoalkylated phenols or 2,4- or 2,6-dialkylphenols can be produced from phenolic compounds in good yields and in the absence of isomers. The starting phenol which has at least two available ortho or para positions unsubstituted is converted to a t-alkylated phenol having at least one ortho or para position unsubstituted. The desired t-alkylated phenolic compound is reacted with an aldehyde having one to four carbon atoms and a secondary aliphatic or alicyclic amine. The reaction is conducted in the liquid phase with a stoichiometric amount of the phenolic compound and stoichiometric or excess of stoichiometric amounts of the aldehyde and the secondary amine. The reaction is conducted at a temperature in the range of about 0° C., to about 100° C. and the reaction produces an aminoalkylated t-alkylated phenol. The aminoalkylated phenol is contacted with hydrogen in the presence of a metal catalyst at a temperature of about 100° C. to about 175° C. at a hydrogen pressure not greater than 500 psi to produce monoalkylated, mono- or di-t-alkylated phenol or a dialkylated, mono-t-alkylated phenol in the ortho- and para- positions. The thus produced alkylated t-alkylated phenolic compound is contacted with an acid or an acid reacting substance to give the desired alkylated phenolic compound. These compounds are separated to produce ortho-monoalkylated, para-monoalkylphenol, 2,4-dialkylphenol and 2,6-dialkylphenol.

27 Claims, No Drawings

PROCESS FOR ALKYLATING PHENOLIC COMPOUNDS TO PRODUCE ORTHO- OR PARA-MONOALKYLATED PHENOLS OR 2,4- OR 2,6-DIALKYLATED PHENOLS

BACKGROUND OF THE INVENTION

This invention relates to a process for producing ortho- or paramonoalkylphenols or 2,4- or 2,6-dialkylphenols. More particularly, the invention relates to an alkylation process for phenols that have at least two replaceable hydrogens in the ortho- or para-position whereby the phenol is first converted to a t-alkylated phenol having at least one hydrogen in the ortho- or para-position. This t-alkylated phenol is reacted with an aldehyde and a secondary amine to form the aminoalkylated phenol that then is subjected to hydrogenolysis to produce an ortho- or para-alkylated, ortho- or para-t-alkylated phenol. The alkylated t-alkylated phenol is then contacted with an acid or acid reacting substance to give the alkylated phenol. Phenolic compounds with alkylated ortho-positions and/or para-positions are useful as various industrial materials. For example, 2,3,6-trimethylphenol is a desirable intermediate in the synthesis of vitamin E.

The method of t-alkylating phenols that have at least two open positions ortho-ortho or ortho-para to the hydroxyl group to form a t-alkylated phenolic compound still having at least one ortho- or para-position open is well known in the art. Thus contacting the phenol having at least two positions open with a branched olefin, a t-alkyl halide or a t-alcohol in the presence of an acidic catalyst is a common industrial practice. Such catalysts may be of the Bronsted type such as sulfuric acid, arylsulfonic acid, m-benzenedisulfonic acid, methanesulfonic acid, ion-exchange resin sulfonic acids or Lewis acids such as aluminum chloride, zinc chloride, magnesium chloride and the like. Alternately, phenoxides of certain metals such as aluminum, titanium, and zirconium have been used as taught by Ecke et al. (U.S. Pat. No. 2,821,898), Leston (U.S. Pat. Nos. 3,331,879; 3,267,153 and 3,267,155) and Hokama (U.S. Pat. No. 3,267,154). Still another way to introduce one or two t-alkyl groups into the nucleus of a phenolic ring is by the total t-alkylation of all the available ortho-para-positions followed by partial de-t-alkylation to obtain the desired partially t-alkylated phenol. Examples of this partial de-t-alkylation are given by Leston (U.S. Pat. Nos. 3,091,646 and 3,346,649), but de-t-alkylation may also be carried out by the convention process with Lewis or Bronstedt acids.

The method of alkylating phenols that have an open ortho- or para-position with an aldehyde and secondary amine to form aminoalkylated phenols that are then cleaved by hydrogenolysis to produce alkylated phenols is well known in the art. An example is U.S. Pat. No. 2,194,215 (Bruson et al.) which teaches the methylation of phenolic compounds by condensing the phenolic compounds with at least one molecular equivalent each of formaldehyde and a strongly basic, non-aromatic secondary amine to form phenolic tertiary amines. The phenolic tertiary amine obtained is then subjected to hydrogenolysis, whereby the secondary amine is reformed and a new methylated phenolic compound is produced. The hydrogenolysis is performed in the presence of the hydrogenation catalyst, copper chromite, at a temperature above 100° C. and below 300° C., and preferably between 150° C. and 200° C. By this process phenol can be converted into ortho-cresol, para-cresol, 2,4-xylenol, 2,6-xylenol or 2,4,6-trimethylphenol or mixtures thereof, depending upon whether one, two or three moles each of formaldehyde and a secondary amine are employed for the condensation.

Many hydrogenation catalysts are known in the art. These catalysts can exist in natural state or in the oxidized state. In referring to the oxidized state of a hydrogenation catalyst, the art generally refers to the oxidized hydrogenating components of the catalyst which are generally selected from the Group VIII metals of the Periodic Table of the elements and include iron, cobalt, nickel, ruthenium, rhodium, palladium, osmium, iridium and platinum. It is also known that these catalysts can be used as hydrogenolysis catalysts for cleaving compounds. An example of the use of some of these catalysts as hydrogenolysis catalysts is given in U.S. Pat. No. 3,946,086 (Gershanov et al.) which teaches a method for producing 2,6-dialkyl and 2,6-diaralkyl substituted derivatives of para-cresol. In this method phenol is alkylated with an olefin having from four to twelve carbon atoms or with styrene at a temperature in the range of 50° C. to 150° C. in the presence of a catalyst, namely, aluminum, to produce 2,6-dialkylphenol or 2,6-diaralkylphenol. The 2,6-dialkylphenol or 2,6-diaralkylphenol resulting from the alkylation is treated at with a mixture of formaldehyde and dimethylamine or with a reaction product thereof having the formula

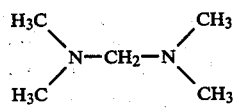

at a temperature of 20° C. to 100° C. to form N,N-dimethyl(3,5-dialkyl-4-hydroxybenzyl)amine or N,N-dimethyl(3,5-diaralkyl-4-hydroxbenzyl)amine. These tertiary amines are subsequently subjected to catalytic hydrogenolysis with either pure hydrogen or a hydrogen-containing gas, such as a methane-hydrogen mixture or a nitrogen-hydrogen mixture. The hydrogenolysis catalysts useful in this teaching are those that are conventionally used for this process, such as nickel, palladium, platinum, and copper. The teaching suggests that it proves more expedient to use a nickel-chromium catalyst, nickel-copper catalyst, and especially, alloyed nickel-aluminum-titanium catalyst. Also, the amination should be carried out in the medium of a saturated aliphatic alcohol such as monobasic aliphatic alcohols having one to four carbon atoms. The amination step must lead to the positioning of the alkyl groups in the para-position since the ortho-position is already occupied in the starting material. The products produced from the process of this teaching are the 2,6-dialkyl and 2,6-diaralkyl substitute derivates of para-cresol.

The final de-t-alkylation may be performed as described above with Bronstedt or Lewis acids or with metal phenoxides.

One skilled in the art is not taught by the aforementioned teaching as to how to produce phenols selectively alkylated in either the ortho- or para-position or di-ortho or di-ortho-para alkylated and having still one or two open ortho- or para-positions.

One skilled in the art is also not taught by the aforementioned teachings as to how to produce para-monoalkylated phenol or para-cresol in good yields and purity from a phenolic compound containing an open ortho- or para-position.

SUMMARY OF THE INVENTION

In accordance with the present invention, there has been discovered a process for producing ortho- or para-monalkylphenols or 2,4- or 2,6-dialkylphenols in good yields and free of isomers from phenolic compounds containing at least two open ortho- or para-positions.

The present invention comprises converting a phenolic compound that has at least two replaceable hydrogens in the ortho-ortho or ortho-para positions to a t-alkylated phenol having at least one replaceable hydrogen in the ortho- or para-position by t-alkylation, transalkylation or partial de-t-alkylation. The t-alkylated phenol having at least one replaceable hydrogen in the ortho- or para-position is reacted with an aldehyde having one to four carbon atoms and a secondary nonaromatic amine to form an aminoalkylated t-alkylated phenolic compound. The aminoalkylation is performed in the liquid phase at a temperature in the range of about 0° C. to about 100° C. with the t-butylated phenol in stoichiometric amounts and the aldehyde and the amine in stoichiometric or in excess of stoichiometric amounts. The aminoalkylated t-alkylated phenolic compound is contacted with hydrogen at a pressure up to about 500 psi and at a temperature in the range from about 100° C. to about 175° C. in the presence of a catalyst. In the case where the aminoalkyl group is ortho to the hydroxyl group, the hydrogenolysis is performed preferably in a glass-lined vessel in the presence of a catalyst selected from the group consisting of palladium, platinum, iridium, rhodium or rubidium. The alkylated phenolic compound is then contacted with an acidic agent to produce in good yields the desired isomerically pure alkylated phenolic compound having at least one replaceable hydrogen in an ortho- or para-position.

DETAILED DESCRIPTION OF THE INVENTION

The phenolic compounds that are useful in the process of this invention are those that contain at least two replaceable hydrogens in both of the ortho-position, or the ortho-para-positions. Specific examples of the phenolic compound used in the process of the present invention include phenol, meta-cresol, ortho-cresol, 2,3-xylenol, 3,4-xylenol, 2,5-xylenol, phenols having substituted thereon one or more alkyl radical groups, such as ethyl, propyl, isopropyl, butyl and the like in one of the ortho positions on the ring and/or in the meta positions on the aromatic ring. Also included are fused ring phenols that as naphthols and similar compounds, as well as polyhydric phenols exemplified by resorcinol, pyrogallol and hydroquinone.

The phenols of this invention may even be composed of mixtures of the desired phenols with other phenols whith ortho phenols such as meta-para cresol; 2,4–2,5-xylenol; 2,3-xylenol admixed with 3,5-xylenol or with 2,3,6- or 2,4,6-trimethylphenol, 3,4-xylenol admixed with 2,3,6- or 2,4,6-trimethylphenol.

The phenolics that are useful in this invention, either pure or admixed with other phenolic compounds, are converted to partially t-alkylated phenolic compounds so that the t-alkylated phenol obtained still contains at least one open ortho- or para-position. This conversion may be accomplished by partial t-alkylation with a tert-alkyl halide or a tertiary alkyl alcohol in the presence of an acid catalyst. Non-limiting examples of such partial t-alkylations are phenol to p-t-alkylphenol; phenol to 2,4-di-t-alkylphenol; o-cresol to 4-t-butyl-o-cresol or to 6-t-butyl-o-cresol; m-cresol to 6-t-alkyl-m-cresol or to 4,6-di-t-alkyl-m-cresol; 2,3-xylenol to 6-t-alkyl-2,3-xylenol; 3,4-xylenol to 6-t-alkyl-3,4-xylenol; ortho-ethylphenol to 6-t-butyl-o-ethylphenol; 2,5-xylenol to 4-t-butyl-2,5xylenol. The desired isomer may be isolated by conventional means such as fractional distillation or crystallization. Such means of separation also apply when starting with mixtures of phenols. An example of such would be the t-alkylation of a mixture of metal and para-cresols to 4,6-di-t-butyl-m-cresol and 2,6-di-t-butyl-p-cresol as well as monobutylated m,p-cresols and separating the desired 4,6-di-t-butyl-m-cresol by distillation. In a similar fashion a 2,4- and 2,5-xylenol mixture may be t-alkylated and the desired 4-t-alkyl-2,5-xylenol may be isolated from 6-t-alkyl-2,4-xylenol and unreacted 2,4- and 2,5-xylenols by distillation. In another example, 2,3-xylenol admixed with 2,4,6-trimethylphenol could be partially t-alkylated to 6-t-alkyl-2,3-xylenol while the 2,4,6-trimethylphenol is unreacted. The desired 6-t-alkyl-2,3, -xylenol may be separated from the mixture by fractional distillation.

The alkylating compounds of the present invention are aldehydes having one to four carbon atoms. Examples of the aldehydes include formaldehyde in aqueous form or in polymeric form, acetaldehyde, propionaldehyde, isopropionaldehyde, n-butyraldehyde, isobutyraldehyde. The preferred aldehyde for use in the present invention is formaldehyde. The secondary amine used in the process of this invention must have sufficient basicity to form the aminoalkylphenol upon reaction with the phenolic compound and the aldehyde. The use of a readily available secondary amine such as dimethylamine, diethylamine, diisopropylamine and piperidine is particularly recommended.

The hydrogenation catalyst used in the process of the present invention in the hydrogenolysis step, where the aminoalkylphenol t-alkyl is cleaved into alkylphenols t-alkyl and the secondary amine, contains the noble metals selected from the group consisting of iridium, palladium, platinum, rhodium and rubidium and mixtures thereof. The metallic components may or may not be deposited on a support, but are generally deposited on an inorganic oxide base or carrier material. Suitable carrier materials are silica aluminas, the crystalline aluminosilicates, alumina, porous or nonporous carbon blacks of small or large specific surface areas, and other carbonaceous materials such as activated carbon, coke, or charcoal and other supporting material like thoria, or kieselguhr. Commercial activated carbons which may be used are available under the trade names of NORIT, NUCHAR, and DARCO, but other similar carbon materials familiar to those skilled in the art may be used. The hydrogenolysis catalyst may be prepared by any conventional method, when used without a support and when used with a support; it may be prepared by any conventional method for impregnating a porous carrier with a metallic component. One such manner is to make a composite of the metal component with the catalyst base by forming an aqueous solution of the halide of the metal such as platinum chloride, palladium chloride, etc., further diluting the solution and adding the resultant diluted solution to the base in a steam dryer. Other suitable metal solutions may be employed such as colloidal solutions or suspensions, including the desirable metal cyanides, metal hydroxides, metal oxides, and metal sulfides, etc. In cases where these solutions are not soluble in water at temperatures used, other suitable solvents such as alcohols, ethers, etc. may be utilized.

In the process of this invention, a typical reaction sequence involved is the following:

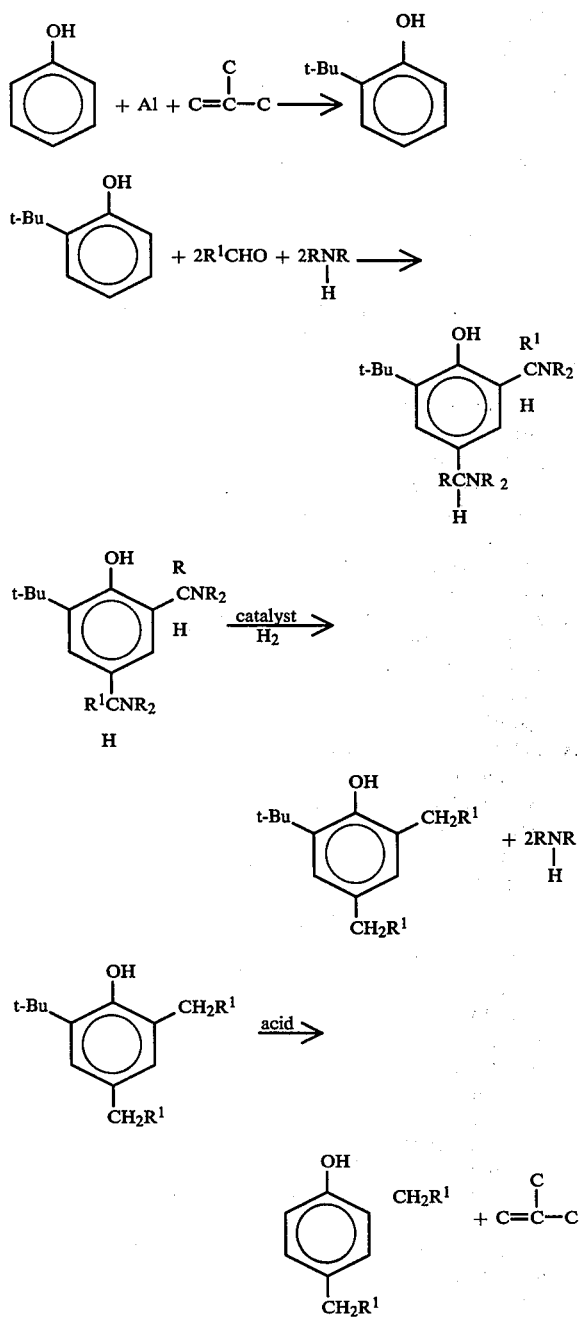

The t-alkylated phenolic compound is mixed with the secondary amine and the aldehyde is added to this mixture, and these compounds are reacted to produce the aminoalkylphenol. This reaction can take place in any vessel known to those skilled in the art for conducting chemical reactions. The suitable mole ratio of the phenolic compound, secondary amine, and aldehyde fed to the reaction vessel is such that phenolic is stoichiometric quantity and the amine and aldehyde are in stoichiometric, twice stoichiometric or excess quantities. This reaction is conducted at a temperature in the range of around 0° C. to around 100° C., but lower temperatures can be used, resulting in a slower and undesirable reaction rate. The reaction is also conducted in the liquid phase and may be conducted in the presence of a solvent. Suitable solvents for use in the process of the invention are lower alkyl alcohols such as methanol, ethanol, propanol, isopropanol, butanol and sec-, iso-, and tert-butanols. The reaction is best carried out until a maximum quantity of the aminoalkylated phenol is produced, but shorter times may be used althout such use would not be desirable from an economic standpoint.

After the water is stripped from the solution or after a sufficient amount of methanol is added to make the mixture of water and aminoalkylated phenol and unreacted reactants a homogeneous mixture and act as a solvent, in order to prevent the water from adversely affecting the catalyst, the aminoalkylated phenol is then subjected to hydrogenolysis by contacting the aminoalkylated phenol with hydrogen. The contacting occurs at a hydrogen pressure no higher than 500 psi and at a temperature in the range of about 0° C. to about 175° C. in the presence of a noble metal catalyst selected from iridium, palladium, platinum, rhodium, or rubidium, or mixtures thereof. The hydrogenolysis may be carried out in a glass-lined vessel to prevent any metals other than the type present in the catalyst from contacting the reactants. The hydrogenolysis cleaves the aminoalkylated t-butylated phenol to produce an alkylated t-alkylated phenol. Also produced is the secondary amine used in the reaction with the phenolic compound and the aldehyde. This secondary amine can be recycled to the reaction vessel where the phenolic compound, secondary amine and aldehyde are reacted. Also, the hydrogenolysis catalyst can be removed from the glass-lined reaction vessel, filtered and recycled for reuse in the glass-lined reaction vessel for further hydrogenolysis.

The alkylated t-alkylated phenolic mixture containing predominantly the para-alkylated phenol after the secondary amine has been removed from the mixture for recycling is treated to a separation step to produce the alkylated t-butylated phenol in a good yield and of a high purity. In the process of the present invention, the alkylated t-alkylated phenolic compounds can be separated from the mixture containing the alkylated t-alkylated phenolic compounds and the secondary amine and the catalyst by any method known to those skilled in the art. This separation step usually includes springing the phenolics from the mixture by acidifying the mixture and extracting the alkylated phenolic compound.

The amount of catalyst used in the hydrogenolysis step is generally between about 0.001 and about 1 percent of the weight of the amino derivatives employed in the reaction. This quantity of palladium is preferentially between about 0.01 and about 0.1 percent by weight of the amino derivatives.

The foregoing process may be carried out as a batch-type, semi-continuous or continuous operation utilizing a fixed or moving bed catalyst system for the aminoalkylation step if a catalyst is used and for the hydrogenolysis step. One embodiment entails the use of a fluidized catalyst zone for a hydrogenolysis step, where, in the glass-lined vessel, the mixture of aminomethylated phenols is passed countercurrently or co-currently through a moving fluidized bed of the palladium on carbon catalyst. The fluidized catalyst, after use, is filtered from the product mixture and is conducted or recycled to the glass-lined vessel for reuse. After the palladium on carbon catalyst has been used for a period of time, it may require regeneration, which can be performed by any method known to those skilled in the art.

The alkylated t-alkylated phenol is then contacted with an acid to remove the t-alkyl group. The preferred method comprises contacting the alkylated t-alkylated phenol with an acid or an acid reacting substance at elevated temperature and removing the t-alkyl as the olefin. Typical nonlimiting examples include the use of Bronstedt acids such as sulfuric acid, benzene sulfonic acid, toluenesulfonic acid, phenolsulfonic acid, cresolsulconic acid, m-benzenedisulfonic acid, methanesulfonic acid and the like and at temperatures generally in the range of about 100° C. to about 350° C. Lewis acids such as $AlCl_3$, $ZnCl_2$, $SnCl_4$, $FeCl_3$ and the like may also be used. Ion-exchange resins of the sulfonic acid type are likewise applicable. Solid catalysts such as alumina, silica-aluminas, acid-activated clays may also be used. Both liquid and vapor phase reactions are useful in the performance of this reaction. Trans-t-alkylation may also be performed wherein the t-alkyl group is removed from the alkylated t-alkylated phenolic compound and transferred to another molecule. This other molecule is usually an aromatic ring and preferably a phenol. It may even be the starting phenol. Such trans-t-alkylations usually take place under milder conditions than de-t-alkylations, typically of 0°–150° C.

It will be understood that in the above described process the hydrogenolysis step and the de-t-alkylation step may be reversed.

Typical nonlimiting examples of processes in which phenolic compounds which have an alkyl group having one or four carbon atoms and still containing one or two hydrogen ortho-ortho or ortho-para in the phenolic ring which phenolic compounds can be produced in good yields and high purity by this invention include the following:

a. Synthesis of 2,3-xylenol from m-cresol and p-cresol.

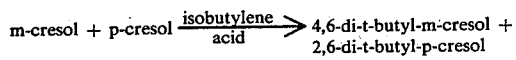 (1)

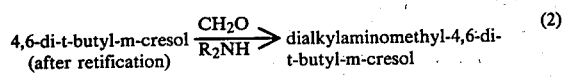 (2)

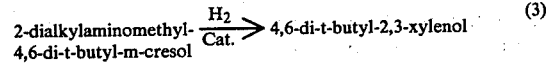 (3)

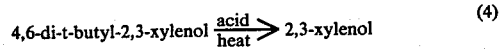 (4)

b. Synthesis of 2,3,4-trimethylphenol from 2,3-xylenol

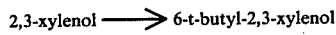 (1)

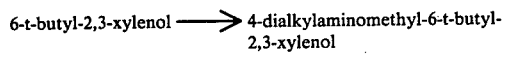 (2)

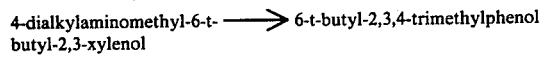 (3)

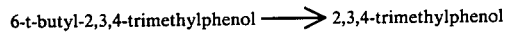 (4)

c. Synthesis of 2,3,6-trimethylphenol from m-cresol

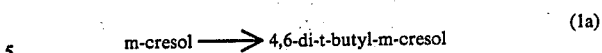 (1a)

 (1b)

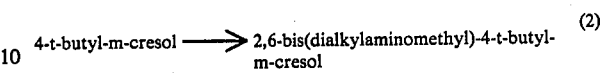 (2)

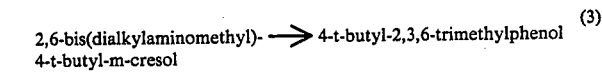 (3)

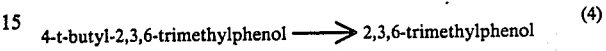 (4)

The invention is more completely described with reference to the example below.

EXAMPLE 1

A solution of 16.4 g. (0.10 mole) of 4-t-butyl-m-cresol (Bp. 172.2–172.6/50 mm Hg) in 50 ml of methanol was prepared. To this 45.1 g. (0.25 mole) of 25 percent aqueous dimethylamine was added. Next, 20.25 g. (0.25 mole) of 37 percent aqueous formaldehyde was added dropwise with stirring and cooling. This took 20 minutes at 26°–31° C. Seventy millilites of methanol was added and 2.3 g of 5 percent Pd/C powder and the product was hydrogenated at 120° C. and 250 psig in a glass-lined autoclave during four hours. The catalyst was filtered and a portion of the filtrate was boiled down on a steam bath to remove methanol. The organic material was extracted with several portions of hexane and the hexane was boiled off on a steam bath. The residue, about 6 g., was refluxed for about one hour with two drops of concentrated sulfuric acid. The product was analyzed by gas chromatography and showed 2,5-xylenol and 2,3,6-trimethylphenol and minor amounts of m-cresol and 2,3-xylenol.

EXAMPLE 2

A solution of 6-t-butyl-2,3-xylenol, 17.8 g (0.10 mole) in 50 ml of methanol is prepared and 18.3 g (0.25 mole) of diethylamine is added. The mixture is stirred at about 20° C. and 11.0 g (0.25 mole) of cold acetaldehyde is added slowly below the liquid surface over a period of one hour. The mixture is then distilled to remove unreacted aldehyde and amine and the methanol solvent. Next, 3 g of 13% silica-alumina catalyst (Davison Chemical Co.) is added to the residual mixture and the resultant mixture is slowly heated to 250° C. to effect the de-t-butylation. The residue after the evolution of gas ceases is dissolved in 100 ml of methanol. The silica-alumina catalyst is separated by filtration and the methanolic solution is introduced into a glass-lined autoclave along with 3 g of 5% $Pd/Al_2O_3$. The hydrogenation is performed at 120° C. and 250 psig during three hours. The hydrogenation catalyst is then removed by filtration and the methanol is removed on a steam bath leaving 4-ethyl-2,3-xylenol containing a minor amount of 2,3-xylenol.

It will be appreciated that a process has been described for producing phenols selectively alkylated in either the ortho- or para-position or being di-ortho or di-ortho-para alkylated and still having one or two open ortho- or para-positions. It will also be appreciated that a method has been described for producing para-monoalkylated phenol or para-cresol in good yields and purity from a phenolic compound containing an open ortho- or para-position. Although the invention has been described with a certain degree of particularly, it is to be understood that the present disclosure has been made only as an example and that the scope of the invention is defined by what is claimed hereafter.

What is claimed is:

1. A process for alkylating a phenolic compound having from about six to about ten carbon atoms and having at least two hydrogens in the ortho-ortho or ortho-para positions to produce another phenolic compound having one or two alkyl groups in the ortho or para or ortho-ortho or ortho-para positions comprising:
    (a) converting the phenolic compound to a mono- or di-t-alkylated phenol derivative which still has one or two hydrogens in the ortho, para, ortho-ortho or ortho-para positions;
    (b) reacting the t-alkylated compound formed in step (a) with a saturated aliphatic aldehyde having one to four carbon atoms and a secondary non-aromatic amine having two to about eight carbon atoms, wherein the amount of the t-alkylated phenolic compound is a stoichiometric amount and the amounts of the aldehyde and amine are at least stoichiometric amounts, and at a temperature in the range of about 0° C. to about 100° C. to produce a Mannich base type aminoalkylated t-alkylated phenolic compound;
    (c) contacting the Mannich base type aminoalkylated t-alkylated phenolic formed in step (b) with hydrogen in the presence of a hydrogenation catalyst to produce an alkylated t-alkylated phenolic compound; and
    (d) contacting the alkylated t-alkylated phenolic compound formed in step (c) with an acid or an acid reacting substance at a temperature from about 25° C. to about 300° C. to produce a phenolic compound which is selected from the group consisting of a monoalkylated phenolic compounds alkylated in the ortho- or para-positions and dialkylated phenolic compounds alkylated in the ortho-ortho, ortho- or ortho-para-positions and having at least one ortho- or para-position unsubstituted.

2. A process for alkylating a phenolic compound having from about six to about ten carbon atoms and having at least two hydrogens in the ortho-ortho or ortho-para positions to produce another phenolic compound having one or two alkyl groups in the ortho or para or ortho-ortho or ortho-para positions comprising:
    (a) converting the phenolic compound to a mono- or di-t-alkylated phenol derivative which still has one or two hydrogens in the ortho, para, ortho-ortho or ortho-para positions;
    (b) reacting the t-alkylated compound formed in step (a) with a saturated aliphatic aldehyde having one to four carbon atoms and a secondary non-aromatic amine having two to about eight carbon atoms, wherein the amount of the t-alkylated phenolic compound is a stoichiometric amount and the amounts of the aldehyde and amine are at least stoichiometric amounts, and at a temperature in the range of about 01° C. to about 100° C. to produce a Mannich base type aminoalkylated t-alkylated phenolic compound;
    (c) contacting the aminoalkylated t-alkylated phenolic compound formed in step (b) with an acid or an acid reacting substance at a temperature from about 25° C. to about 300° C. to produce an aminoalkylated phenolic compound which is selected from the group consisting of aminoalkylated phenolic compounds, aminoalkylated in the ortho- or para-positions and diaminoalkylated phenolic compounds aminoalkylated in the ortho-ortho, ortho or ortho-para positions and having at least one ortho- or para-position unsubstituted; and
    (d) contacting the Mannich base type aminoalkylated phenol compound formed in step (c) with hydrogen in the presence of a hydrogenation catalyst to produce an alkylated phenolic compound having at least one ortho- or para-position unsubstituted.

3. A process for alkylating a mono- or di-t-alkylated phenolic compound having from about ten to about twenty four which has two hydrogens in the ortho, para, ortho-ortho or ortho-para positions comprising:
    (a) reacting the t-alkylated phenolic compound with a saturated aliphatic aldehyde having one to four carbon atoms and a secondary non-aromatic amine having two to about eight carbon atoms, wherein the amount of the t-alkylated phenolic compound is a stoichiometric amount and the amounts of the aldehyde and amine are at least stoichiometric amounts, and at a temperature in the range of about 0° C. to about 100° C. to produce a Mannich base type aminoalkylated t-alkylated phenolic compound;
    (b) contacting the Mannich base type aminoalkylated t-alkylated phenolic compound formed in step (a) with hydrogen in the presence of a hydrogenation catalyst to produce an alkylated t-alkylated phenolic compound; and
    (c) contacting the alkylated t-alkylated phenolic compound formed in step (b) with an acid or an acid reacting substance at a temperature from about 25° C. to about 300° C. to produce a phenolic compound which is selected from the group consisting of monoalkylated phenolic compounds alkylated in the ortho- or para-positions and dialkylated phenolic compounds alkylated in the ortho-ortho, ortho or ortho-para positions and having at least one ortho- or para-position unsubstituted.

4. A process for alkylating a mono- or di-t-alkylated phenolic compound having from about ten to about twenty four carbon atoms and which has two hydrogens in the ortho, para, ortho-ortho or ortho-para positions comprising:
    (a) reacting the t-alkylated compound with a saturated aliphatic aldehyde having one to four carbon atoms and a secondary non-aromatic amine having two or about eight carbon atoms, wherein the amount of the t-alkylated phenolic compound is a stoichiometric amount and the amounts of the aldehyde and amine are at least stoichiometric amounts, and at a temperature in the range of about 0° C. to about 100° C. to produce a Mannich base type aminoalkylated t-alkylated phenolic compound;
    (b) contacting the aminoalkylated t-alkylated phenolic compound formed in step (a) with an acid or an acid reacting substance at a temperature from about 25° C. to about 300° C. to produce an aminoalkylated phenolic compound which is selected from the group consisting of aminoalkylated phenolic compounds, aminoalkylated in the ortho- or para-positions and diaminoalkylated phenolic compounds aminoalkylated in the ortho-ortho, ortho or ortho-para positions and having at least one ortho- or para-position unsubstituted; and (c) contacting the Mannich base type aminoalkylated phenol compound formed in step (b) with hydrogen in the presence of a hydrogenation catalyst to produce an alkylated phenolic compound having at least one ortho- or para-position unsubstituted.

5. The process according to claim 3 wherein the Mannich base type aminoalkylated phenolic compound is contacted with hydrogen in a glass-lined vessel.

6. The process according to claim 5 wherein the Mannich base type aminoalkylated phenolic compound is contacted with hydrogen in the presence of a noble metal catalyst selected from a group consisting of palladium, platinum, rubidium, rhodium, indium and mixtures thereof.

7. The process according to claim 6 wherein the Mannich base type aminoalkylated phenolic compound is contacted with hydrogen at a pressure less than 500 psig and at a temperature in the range of about 100° C. to about 140° C.

8. The process according to claim 3 wherein the separated secondary amine is recycled to be reacted with the t-alkylated phenolic compound and aldehyde.

9. The process according to claim 6 wherein the noble metal catalysts are supported on materials selected from the group consisting of porous or non-porous carbon blacks, or silica.

10. The process according to claim 3 wherein the catalyst is filtered from the reaction product and recycled to the hydrogenolysis reaction.

11. The process according to claim 3 wherein the amine is added to the t-alkylated phenolic compound before the aldehyde is added.

12. The process according to claim 3 wherein the reacting of the t-alkylated phenolic compound with the amine and the aldehyde is performed in methanol.

13. The process according to claim 3 wherein the catalyst used for the hydrogenation is a palladium on carbon catalyst.

14. The process according to claim 3 wherein the t-alkylated phenolic compound is a t-butylated phenolic compound.

15. The process according to claim 3 wherein the aldehyde used is formaldehyde.

16. The process according to claim 14 wherein the formaldehyde used is a 37 percent aqueous formaldehyde solution.

17. The process according to claim 14 wherein the formaldehyde used is paraformaldehyde.

18. The process according to claim 3 wherein the secondary nonaromatic amine is selected from a group consisting of dimethylamine, diethylamine, diisopropylamine and piperidine.

19. The process according to claim 3 wherein the t-alkylated phenolic compound is 4-t-butyl-m-cresol and the aldehyde is formaldehyde and the final product is 2,3,6-trimethylphenol.

20. The process according to claim 3 wherein the t-alkylated phenolic compound is 6-t-butyl-m-cresol, the aldehyde is formaldehyde and the final phenolic compound is 2,3,4-trimethylphenol.

21. The process according to claim 3 wherein the t-alkylated phenolic compound is 4-t-butyl-2,5-xylenol, the aldehyde is formaldehyde and the final phenolic product is 2,3,6-trimethylphenol.

22. The process according to claim 3 wherein the t-alkylated phenolic compound is 6-t-butyl-2,3-xylenol, the aldehyde is formaldehyde and the final phenolic compound is 2,3,4-trimethylphenol.

23. The process according to claim 3 wherein the amine is separated from the mixture by contacting the mixture with an acid and then extracting the phenolic compounds with an organic water-immiscible solvent.

24. The process according to claim 3 wherein the secondary amine is selected from the group consisting of dimethylamine or diethylamine.

25. The process according to claim 1 wherein step (a) is carried out by t-alkylation.

26. The process according to claim 1 wherein step (a) is carried out by trans alkylation.

27. The process according to claim 1 wherein step (a) is carried out by partial de-t-alkylation.

* * * * *